United States Patent [19]
Slilaty et al.

[11] Patent Number: 6,127,171
[45] Date of Patent: Oct. 3, 2000

[54] CLONING VECTOR CONTAINING MARKER INACTIVATION SYSTEM

[75] Inventors: Steve N. Slilaty; Suzanne Lebel, both of Laval, Canada

[73] Assignee: Genomics One Corporation, Laval, Canada

[21] Appl. No.: 09/070,842

[22] Filed: May 1, 1998

Related U.S. Application Data

[63] Continuation-in-part of application No. 08/852,834, May 7, 1997, abandoned.

[51] Int. Cl.$^7$ ............................ C12N 15/65; C12N 15/66; C12Q 1/02
[52] U.S. Cl. ...................... 435/320.1; 435/29; 435/91.41; 435/471
[58] Field of Search ................................ 435/6, 29, 91.4, 435/91.41, 471, 472, 474, 475, 476, 488, 252.33, 320.1; 536/23.1, 23.7

[56] References Cited

U.S. PATENT DOCUMENTS 5,474,933  12/1995  Weiner et al. .................. 435/252.3

OTHER PUBLICATIONS

Heinrich et al. Positive–selection vector with enhanced lytic potential based on a variant of pX174 phage gene E. Gene 154: 51–54, Mar. 1995.

Shizuya et al. Cloning and stable maintenance of 300–kilobase–pair fragments of human DNA in *Escherichia coli* using an F–factor–based vector. Proc. Natl. Acad. Sci. USA 89: 8794–8797, Sep. 1992.

Sambrook et al., 1989, "Molecular Cloning: A laboratory manual", second edition. Cold Spring Harbor Laboratory Press, pp. 1.8,1.9,1.13,1.14,1.53–1.59,1.85,1.86, and 4.7–4.11.

Zabin, "B–Galactodidase α–complementation", 1982, Molecular and Cellular Biochemistry, vol. 49, pp. 87–96.

Dunn et al., "Improved Peptide function from random mutagenesis over short 'windows'", 1988, Protein Engineering, vol. 2, No. 4, pp. 283–291.

*Primary Examiner*—David Guzo
*Assistant Examiner*—Thomas G. Larson
*Attorney, Agent, or Firm*—Hodgson, Russ, Andrews, Woods & Goodyear, LLP

[57] ABSTRACT

Provided are lacZα gene fragments which have been modified to introduce multiple restriction enzyme sites. Vectors according to the present invention include at least one promoter operatively linked to a DNA sequence encoding lacZα (α-peptide); multiple cloning sites cleavable by distinct restriction enzymes which have been introduced within a lacZ coding sequence from and including the codon for amino acid 8, and in the lacZ coding sequence downstream of the codon for amino acid 8, in forming the modified lacZα coding sequence; and a replicon. The vector may further comprise one or more additional features useful for protein expression and other molecular manipulations. Also provided are methods of using the vectors wherein a DNA molecule is cloned into at least one restriction enzyme site in the modified lacZα coding sequence, in forming recombinant vectors; introducing the recombinant vectors into competent host cells; growing the host cells in the presence of a chromogenic substrate cleavable by β-galactosidase; and screening for indicia of lac operon marker inactivation. The high accuracy of color selection afforded by the modified lacZα coding sequence of the present invention provides a first opportunity at performing gap-free shotgun sequencing and development of ordered genomic libraries.

29 Claims, 8 Drawing Sheets

```
            5                    10
M   T   M   I   T   D   S   L   A   V
ATGACNATGATHACNGAYEEELLLGCNGTN
        TGATCA(BclI)  GCTAGC(NheI)
                             AGTACT(ScaI)
                  GCTNAGC(EspI)

15                   20
V   L   Q   R   R   D   W   E   N   P
GTNLLLCAPRRRRRRGAYTGGGAPAAYCCN
      TTGCAA(Unknown)        CCCGGG(SmaI)
      CTGCAG(PstI)           CCCGGG(SmaI)
            TCGCGA(NruI)

25                   30
G   V   T   Q   L   N   R   L   A   A
GGNGTNACNCAPLLLAAYRRRLLLGCNGCN
         CAATTG(MunI)       TGCGCA(FspI)
         CAGCTG(PvuII)
                ACCGGT(AgeI)
                ATCGAT(ClaI)
                    GCTAGC(NheI)

35                   40
H   P   P   F   A   S   W   R   N   S
CAYCCNCCNTTYGCNEEETGGRRRAAYEEE
         TCGCGA(NruI)  GAATTC(EcoRI)
         TTGCAA(Unknown)
             GCTAGC(NheI)
                 CAGCTG(PvuII)
```

Fig. 1

```
                       45                        50
      E   E   A   R    T   D   R   P   S         Q
   GAPGAPGCNRRRACNGAYRRRCCNEEECAP
          GCGCGC(BssHII)
                CGTACG(Pfl23II)
                      CGATCG(PvuI)
                            AGGCCT(StuI)
                               CGGCCG(Eco52I)

55                         60
      Q   L   R   S    L   N   G   E   W         R
   CAPLLLRRREEELLLAAYGGNGAPTGGRRR
   CAATTG(MunI)
   CAGCTG(PvuII)
       TCCGGA(Kpn2I)
       TGCGCA(FspI)
       TTCGAA(AsuII)
       TACGTA(SnaBI)
           AGATCT(BglII)
            CGATCG(PvuI)
               AAGCTT(HindIII)
                  TTTAAA(DraI)
```

Fig. 1 (continued)

lac Promoter

...TGTGTGGAATTGTGAGCGGATAACAATTTCACACAGGAAACAGCT ATG ACC ATG ATC ACG GAC AGC TTA GCC GTC
　　　　　　　　　　　　　　　　　　　　　SD　　　MET Thr MET Ile Thr Asp Ser Leu Ala Val
　　　　　　　　　　　　　　　　　　　　　　　　　1　　　　　　　　　　　　　　　　　　　10
　　　　　　　　　　　　　　　　　　　　　　　　　↑
　　　　　　　　　　　　　　　　　　　　　　　　6073
　　　　　　　　　　　　　　　　　　　　　　　　　　　　　　　Bcl　　　　　　　Espl Val Leu Gln Arg Arg Asp Trp Glu Asn Pro Gly Val Thr Gln Leu Asn Arg Leu Ala Ala His Pro Pro Phe Ala Ser Trp
GTT CTT CAG CGT CGC GAC TGG GAA AAC CCG GGC GTT ACC CAA TTG AAT CGA TTA GCT GCG CAT CCC CCA TTC GCT AGC TGG
　　　Pstl　　Nrul　　　　　　　　　　　　　Smal/Xmal　　　Munl　　Clal　　　　　　Fspl　　　　　　　Nhel
　　　　　　　　　　　　　20　　　　　　　　　　　　　　　　　　30

Color Selection Cloning Sites

Arg Asn Ser Glu Glu Ala Arg Thr Asp Arg Pro Ser Gln Gln Leu Arg Ser *Readthrough Amino Acids...(70 Additional)*
CGG AAT TCC GAA GAG GCG CGC ACC GAT AGG CCT CAA CAG TTG AGA TCT GAG GCC GAT ACT GTC CCC TCA AAC TGG CAG ATG CAC...
　　EcoRI　　　　　　BssHII　　　　　　Stul　　　　　　　　BglII
　　　　　　　　　　　　　　　　　　　　　　　　　　　　　　↑
　　40　　　　　　　　　　　　　　　　50　　　　　　　　　6234　　54

Fig. 3B

CLONING VECTOR CONTAINING MARKER INACTIVATION SYSTEM

This application is a continuation-in-part of U.S. patent application Ser. No. 08/852,834, filed on May 7, 1997, now abandoned, which is incorporated herein by reference.

FIELD OF THE INVENTION

This invention relates to cloning systems using marker inactivation for the identification of recombinants containing the insertion of a nucleic acid molecule. More particularly, the present invention relates to lacZα gene fragments having improved accuracy and reliability in detecting the insertion of a nucleic acid molecule therein.

BACKGROUND OF THE INVENTION

The industrial applications of genetic engineering are becoming evident in the production of pharmaceuticals, of foods having improved properties, and of chemical products (including enzymes) to facilitate manufacturing processes. The process of genetic engineering may begin by cloning a gene of interest which encodes a protein with the desired properties for the particular industrial application. Typically, cloning a gene is done by either breaking up a genome into manageable sized fragments, or generating cDNA fragments from isolated mRNA, and then cloning those genomic or cDNA fragments into a vector and introducing the resultant recombinant vectors into a competent host cell. Commonly used methods for screening transformants, to identify a transformant that contains a recombinant vector with a nucleic acid molecule inserted therein, include marker inactivation systems, including marker inactivation systems which utilize various indicator on reporter genes including lacZ or lacZα, galK, the gene for chloramphenicol acetyltransferase, the gene for the green fluorescent protein (GFP) and mutant forms thereof (see Cubitt et al, 1995, *Trends in Biochem.* 20:448–455), the gene for luciferase and the like; and positive selection systems which utilize lethal genes including ccdB (Bernard et al., 1994, *Gene* 148:71–74), the gene for mouse transcription factor GATA-1 (Trudel et al., 1996, *BioTechniques* 20:684–693), the gene for thymidine kinase, the gene for β-lactamase and the like.

The lac operon marker inactivation system, is employed in one of the most widely used color selection systems for plasmids and single-stranded DNA (ssDNA) vectors (see, e.g., Messing et al., 1977, *Proc. Natl. Acad. Sci. USA* 74:3642–3646; Messing et al., 1981, *Nucl. Acids Res.* 9:309–321; Messing, 1983, *Methods Enzymol.* 101:20–78; and Yanisch-Perron et al., 1985, *Gene* 33:103–119). Essentially, the lac operon marker inactivation system functions by intracistronic complementation between the α-peptide encoded by the lacZα gene fragment, and a β-galactosidase molecule that most commonly carries a deletion of amino acids 12 through 42.

lacZα is a gene fragment, comprising the proximal portion of the *Escherichia coli* lacZ gene, which encodes approximately 60 of the amino terminal amino acids of the β-galactosidase polypeptide chain. The encoded product, the "α-peptide", complements the defective activity of the gene product of lacZM15, an allele that carries a spontaneous deletion of the codon for amino acids 12 through 42 of β-galactosidase. Thus, to identify a transformant that contains a recombinant vector with a nucleic acid molecule inserted therein, vector having a cloning site in the lacZα gene fragment is introduced into a host cell expressing a β-galactosidase having a deletion of amino acids 12 through 42. Transformants, presumably containing vector carrying an intact lacZα gene fragment, produce blue colonies or plaques when applied onto media containing a chromogenic β-galactosidase substrate. This is because functional β-galactosidase activity is achieved by complementation between the a-peptide and a β-galactosidase molecule carrying the deletion, thereby cleaving a chromogenic substrate such as 5-bromo-4-chloro-3-indolyl-β-D-galactoside ("X-gal") to produce deep blue dibromodichloroindigo. In contrast, transformants containing vector carrying a lacZα gene fragment having an insertion produce colorless (white) colonies or plaques when similarly plated. Colorless colonies result when the inserted nucleic acid molecule interrupts expression of the lacZα gene fragment so that the complementing α-peptide is not produced.

Currently, all lacZα-based vectors (e.g. Messing et al., 1977, supra; Yanisch-Perron et al., 1985, supra; Guan et al., 1987, *Gene* 67:21–30; Short et al., 1988, *Nucl. Acids Res.* 16:7583–7600; Alting-Mees and Short, 1989, *Nucl. Acids Res.* 17:9494; Evans et al., 1995, *Biotechniques* 19:130–135; and U.S. Pat. No. 4,766,072) employ the same mechanism for color selection. This mechanism involves placement of restriction sites for insertion of a nucleic acid molecule upstream of the codon for amino acid 7 of β-galactosidase, wherein the inserted nucleic acid molecule ("insert") results in interference with the expression, but not the activity, of the lacZ α-peptide. The current marker inactivation configuration has the disadvantage in that problems arise in the detection of recombinant molecules. More specifically, false positives (white colonies or plaques containing vector not having an insert) and false negatives (colored colonies or colored plaques containing vector that have an insert) may be generated (see, e.g., Messing, 1983, supra; unpublished observations; and Table 2 herein).

Although false positive results are difficult to eliminate owing to the fact that they arise to a large extent out of factors which are extraneous to the selection system itself, these do not generally constitute a problem since they are selected alongside actual positives and are subjected to further scrutiny before their fate is decided. Among the external factors responsible for generating false positives are (i) contamination of restriction and modification enzymes with exonucleases, polymerases or other restriction enzymes; (ii) spontaneous mutations; and (iii) loss of the F' episome carrying the lacZM15 allele.

False negatives, on the other hand, represent a problem as they are rarely carried forward for further examination and, as a result, are responsible for numerous erroneous conclusions. Such erroneous conclusions include, at least in part, the general phenomenon referred to as "non-clonable sequences", and the presence of an excessive number of gaps in shotgun DNA sequencing results. False negatives are caused by both extrinsic factors, as well as factors which are intrinsic to the architecture of the color selection mechanism itself. In the currently available lacZα-based vectors, there are two principal causes of false negatives: (i) in-frame insertion of DNA fragments containing one or more open reading frames; and (ii) reinitiation of translation within the mRNA transcribed from the inserted DNA fragment at any in-frame AUG, GUG or even UUG and CUG preceded by a pseudo Shine-Delgarno box. Events arising out of either of these two instances result in the synthesis of α-peptides bearing aminoterminal fusions. Since neither amino nor carboxyterminal fusions to the α-peptide usually impair its activity (see, e.g., Slilaty et al., 1990, *Eur. J. Biochem.* 194:103–108), blue colonies or blue plaques indistinguishable from those colonies or plaques produced by vectors not carrying an insert are formed. The number of false negatives produced in like manner is further augmented by the fact that even the less frequent fusions, having diminished levels of α-peptide activity, produce blue colonies or blue plaques due to the hypersensitivity of the X-gal assay system. The hypersensitivity of the X-gal system represents the fact that very little β-galactosidase activity is needed for a complete color-producing reaction to take place.

Hypersensitivity of the X-gal assay system is also responsible for another source of false negatives. This source of false negatives arises as a result of β-galactosidase-like activity produced by the ebg locus of the host cell. The ebg (evolved β-galactosidase) operon is located directly across the chromosome from lacZ and codes for an enzyme that has low level β-galactosidase-like activity (Hall et al., 1989, *Genetics* 123:635–648). In wild-type strains, this enzyme does not have enough activity to allow growth on lactose. However, in typical screening protocols, host cells suspected of being transformants are grown in the presence of an inducer of lacZα gene expression. In such circumstances, the enzyme typically having a low level β-galactosidase-like activity has enough activity in the presence of such inducers (e.g., isopropyl thiogalactoside or "IPTG") to cleave the chromogenic substrate X-gal, thus yielding bluish colonies, or more frequently white colonies with blue centers (unpublished observations). The effects of the ebg locus on blue color formation, in colonies that otherwise would be white, may be minimized by avoiding long incubation periods of plated cells (less than 18 hours), or completely eliminated by using hosts carrying a defective ebg locus.

Thus, there is a need for a cloning vector utilizing the lacZα marker inactivation system, wherein the cloning vector is based on a configuration which minimizes the generation of false negatives. Such a novel cloning vector allows for improved accuracy and reliability in detecting the inactivation of the lacZα gene fragment caused by insertion of a nucleic acid molecule. The novel cloning vector may be used for general cloning purposes, as well as for gap-free shotgun sequencing, in facilitating industrial applications of gene isolation, genetic engineering and development of ordered genomic libraries.

SUMMARY OF THE INVENTION

In accordance with the present invention, disclosed is a marker inactivation system which utilizes lacZα in a configuration which minimizes the generation of false negatives during screening processes for recombinant clones.

In the development of the vector according to the present invention, it was an unexpected result to find that accurate and reliable inactivation of lacZα occurs only when a nucleic acid molecule is inserted in the region of the lacZα gene fragment that encodes amino acids 8 to 38 of β-galactosidase. Thus, of the amino acids encoded by a lacZα gene fragment, residues corresponding to amino acids 8 to 38 of β-galactosidase have been found to be required for functional α-peptide activity for complementation in vivo.

Thus, in one embodiment of the present invention, the vector has at least one promoter operatively linked to a DNA sequence encoding an α-peptide, wherein the resultant α-peptide is capable of complementation with a defective β-galactosidase molecule (e.g. one that carries a deletion of the amino acids 12 through 42) thereby resulting in β-galactosidase activity. At least one cloning site, and preferably multiple cloning sites cleaved by distinct restriction enzymes, is included within the region of the DNA sequence encoding the α-peptide, wherein the region corresponds to the DNA encoding amino acids 8 to 38 of β-galactosidase as shown in SEQ ID NO:1. As appreciated by one skilled in the art from the disclosure of the present invention, modifying the wild type lacZα gene fragment to encode functional α-peptides having altered codons as well as conservative and/or nonconservative substitutions included within, but not limited to, the region of amino acids 8 to 38 of β-galactosidase, can produce DNA sequences with one or more restriction enzymes sites contained therein. Additional embodiments of the present invention include the inclusion in the vector of other features useful for protein expression and other molecular manipulations including, but not limited to, DNA sequences selected from the group consisting of one or more antibiotic resistant genes or auxotrophic genes to aid in selection of recombinants, a ribosome binding site, regulatory elements, at least one origin of replication ("replicon"), a transcription terminator, at least one phage promoter, a phage origin of replication and combinations thereof. Those skilled in the art will recognize that the teachings provided herein can readily be applied to indicator, marker, reporter, or positive selection genes other than lacZ or lacZα to produce cloning vectors which minimize the generation of false negatives during screening processes for recombinant clones as detailed herein for lacZα.

A preferred plasmid vector constructed in accordance with the present invention, designated pTrueBlue™, was constructed using commercially available plasmids, and using standard methods known to those skilled in the art including restriction enzyme digestion, and site-directed mutagenesis.

A preferred phage vector constructed in accordance with the present invention, designated M13TrueBlue™, was constructed using commercially available phage, and using standard methods known to those skilled in the art including restriction enzyme digestion, and site-directed mutagenesis.

A preferred bacterial artificial chromosome vector constructed in accordance with the present invention, designated TrueBlue-BAC™, was constructed using commercially available vector and using standard methods known to those skilled in the art including enzyme digestions and ligations.

The vector according to the present invention is utilized by cleaving the vector with at least one restriction enzyme that is specific to at least one selected restriction site which has been introduced in the region corresponding to the DNA encoding amino acids 8 to 38 of β-galactosidase as illustrated in SEQ ID NO:1. A nucleic acid molecule is then cloned into the cleaved vector. The resultant recombinant vectors are introduced into competent host cells, and transformed host cells are then selected for and screened by growth in the presence of a chromogenic substrate (e.g., X-gal or MacConkey agar) which can be acted upon by β-galactosidase. Clones containing vector carrying an intact lacZα gene fragment produce colored colonies or plaques when grown in the presence of media containing a chromogenic β-galactosidase substrate. Clones containing vector carrying a lacZα gene fragment according to the present invention and having an insertion therein produce colorless (white) colonies or plaques when similarly plated.

In a further embodiment of the plasmid vector according to the present invention, the plasmid vector has been designed to provide capabilities for in vitro preparation of RNA probes, creation of nested deletions through ExoIII protection sites, manipulation of large DNA inserts via sites for 8-base cleaving restriction enzymes, preparation of ssDNA, and protein expression.

These and other objects, features, and advantages of the present invention will become apparent from the following drawings and detailed description.

BRIEF DESCRIPTION OF THE DRAWINGS

FIG. 1 illustrates the first 60 amino acids of β-galactosidase and some of the possible palindromes or restriction enzyme sites which may be introduced into a region of the lacZα coding sequence. The amino acid sequence is disclosed in SEQ ID NO:1.

FIG. 3B is an enlarged view of a region contained within the phage construct shown in FIG. 3A, illustrating multiple cloning sites within a region of the lacZα coding sequence (see bracket labeled "Color Selection Cloning Sites"; This sequence is disclosed is disclosed as SEQ ID NO:10. The amino acid sequence is amino acids 1–54 of SEQ ID NO:1.

DETAILED DESCRIPTION OF THE INVENTION

Definitions

Figure 2A:
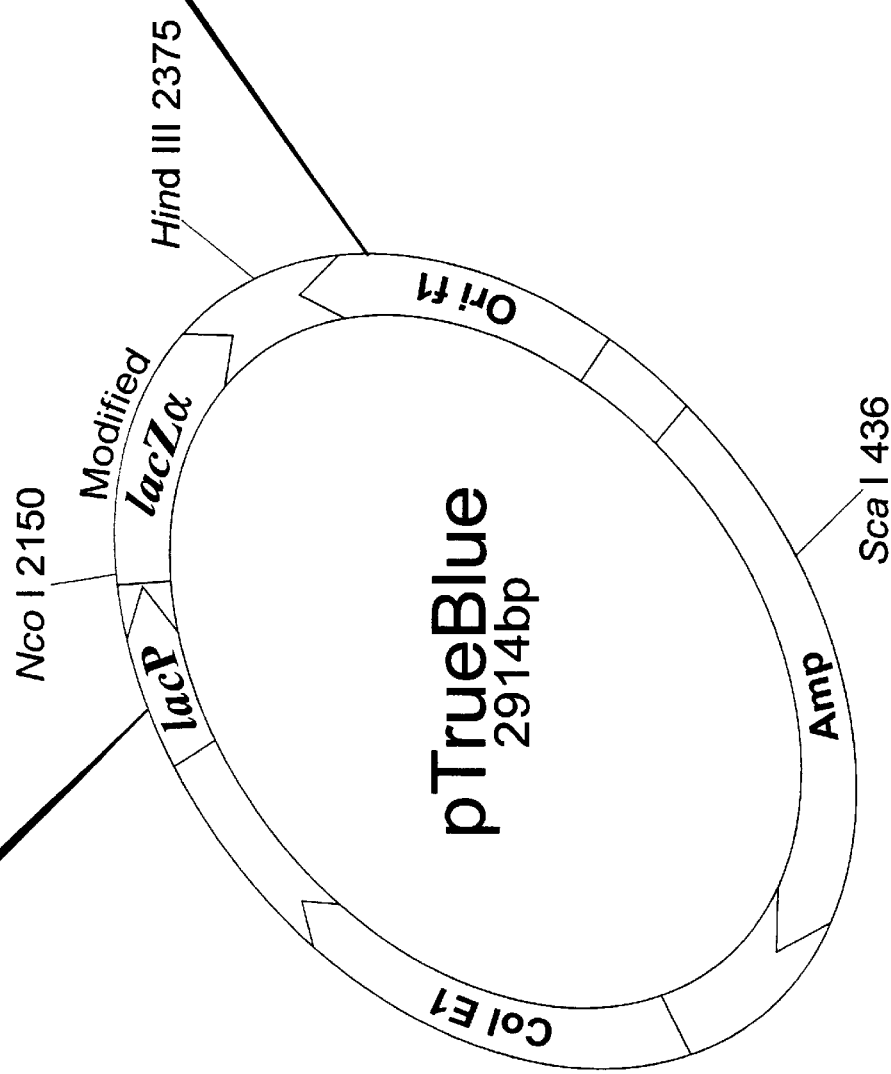
FIG. 2A is a schematic illustration of an embodiment of a plasmid construct according to the present invention.

By the term "α-peptide", is meant, for the purposes of the specification or claims, a peptide that is capable of complementing a defective β-galactosidase molecule (e.g. one having a deletion of amino acids 12 through 42, or amino acids 24–32) such that functional β-galactosidase activity is achieved. While the α-peptide typically used in vivo comprises the first 60 amino acids of the amino terminus of the β-galactosidase molecule, an α-peptide may comprise more or less than 60 amino acids. For example, the minimal purified peptide fragment capable of α-complementation in vitro encompasses a peptide of 39 amino acids comprising amino acids 4 to 42 (Welply et al., 1981, *J. Biol. Chem.* 256:6804–6810). Longer fragments of β-galactosidase, including theoretically the full-length β-galactosidase chain, are also functional as α-peptides (e.g. Slilaty et al., 1990, supra). Additionally, the α-peptide may contain conservative substitutions of the amino acid sequence shown in SEQ ID NO:1. A conservative substitution of one or more amino acids are such that the folding of the α-peptide, and the ability for α-complementation, are substantially unchanged. "Conservative substitutions" is defined by aforementioned function, and includes substitutions of amino acids having substantially the same charge, size, hydrophilicity, hydrophobicity, and/or aromaticity as the amino acid replaced. Such substitutions, known to those of ordinary skill in the art, include, but are not limited to glycine-alanine-valine; isoleucine-leucine; tryptophan-tyrosine; aspartic acid-glutamic acid; arginine-lysine; asparagine-glutamine; and serine-threonine. Also, the α-peptide may contain nonconservative substitutions of the amino acid sequence shown in SEQ ID NO:1. A "nonconservative substitution" is defined as the substitution of any one amino acid for any one or more amino acids such that the α-peptide retains the ability for α-complementation and color production in cloning processes. Nonconservative substitutions are known in the art for the α-peptide, as described in Dunn et al. (1988, *Protein Engineering* 2:283–291; herein incorporated by reference), and may be produced using mutagenic procedures such as described herein.

By the terms "lacZα", "lacZα gene fragment" or "lacZα coding sequence" is meant, for the purposes of the specification or claims to refer to a DNA sequence which encodes an α-peptide as defined above. In that regard, and as appreciated by those skilled in the art, because of codon and third base degeneracy, almost every amino acid can be represented by more than one triplet codon in a coding nucleotide sequence. Thus, there are multiple sequences comprising a lacZα coding sequence, which when compared to each other are modified slightly in sequence (e.g., substitution of a nucleotide in a triplet codon), and yet still encode the α-peptide. By the term "modified lacZα gene fragment" or "modified lacZα coding sequence" is meant, for the purposes of the specification or claims to refer to a DNA sequence which encodes an α-peptide, and which contains one or more cloning sites introduced into and contained in the coding sequence for α-peptide amino acids corresponding to amino acid 8 and downstream of amino acid 8 and particularly corresponding to amino acids 8 to 38 of β-galactosidase.

By the term "β-galactosidase" is meant, for the purposes of specification and claims, to refer to wild-type or naturally occurring β-galactosidase enzyme encoded by the lacZ gene of *E.coli* and other bacteria. In that regard and for the purpose of specification and claims, all references to codon or amino acid numbers in connection with the α-peptide, lacZα, lacZα gene fragment, lacZα coding sequence, or modified lacZα coding sequences are to codons or amino acids that correspond to their counterparts in the standard lacZ gene or the wild-type β-galactosidase sequences.

By the term "six-base palindrome" is meant for the purposes of specification and claims to refer to a double-stranded DNA sequence of six nucleotides that is the same when either of the strands are read in a defined direction. Thus, six base palindrome includes any of the following 64 possible sequences:

| | | | | | | | |
|---|---|---|---|---|---|---|---|
| AAATTT, | AACGTT, | AAGCTT, | AATATT, | ACATGT, | ACCGGT, | ACGCGT, | ACTAGT, |
| AGATCT, | AGCGCT, | AGGCCT, | AGTACT, | ATATAT, | ATCGAT, | ATGCAT, | ATTAAT, |
| CAATTG, | CACGTG, | CAGCTG, | CATATG, | CCATGG, | CCCGGG, | CCGCGG, | CCTAGG, |
| CGATCG, | CGCGCG, | CGGCCG, | CGTACG, | CTATAG, | CTCGAG, | CTGCAG, | CTTAAG, |
| GAATTC, | GACGTC, | GAGCTC, | GATATC, | GCATGC, | GCCGGC, | GCGCGC, | GCTAGC, |

-continued

| | | | | | | | |
|---|---|---|---|---|---|---|---|
| GGATCC, | GGCGCC, | GGGCCC, | GGTACC, | GTATAC, | GTCGAC, | GTGCAC, | GTTAAC, |
| TAATTA, | TACGTA, | TAGCTA, | TATATA, | TCATGA, | TCCGGA, | TCGCGA, | TCTAGA, |
| TGATCA, | TGCGCA, | TGGCCA, | TGTACA, | TTATAA, | TTCGAA, | TTGCAA, | TTTAAA |

By the term "operably linked" is meant, for the purposes of the specification and claims to refer to the chemical fusion, ligation, or synthesis of DNA such that a promoter-DNA sequence combination is formed in a proper orientation and reading frame for the DNA sequence to be transcribed into functional RNA and expressed as a protein or a peptide. Transcription from the promoter-DNA sequence may or may not be regulated by the promoter, and possibly in combination with other regulatory elements. In the construction of the promoter-DNA sequence combination, it is generally preferred to position the promoter at a distance upstream from the initial codon of the DNA sequence that is approximately the same as the distance between the promoter and the gene it controls in its natural setting. However, as known in the art, substantial variation in the distance can be accommodated without loss of promoter function.

By the term "DNA molecule" is meant, for the purposes of the specification and claims to refer to any nucleic acid sequence including, but not limited to, a gene or a gene fragment, natural or synthetic DNA, coding or noncoding DNA, DNA complementary to RNA and so on. The expressed proteins or peptides may include biologically-active, and/or commercially valuable molecules known to those skilled in the art.

By the term "introduction" when used in reference to a host cell is meant, for the purposes of the specification and claims to refer to standard procedures known in the art for introducing recombinant vector DNA into the target host cell. Such procedures include, but are not limited to, transfection, infection, transformation, natural uptake, and electroporation.

By the term "promoter" is meant, for the purposes of the specification and claims to refer to a nucleotide sequence, natural or synthetic, capable of binding RNA polymerase to initiate transcription. Such promoters are known to those skilled in the art and may include bacterial, yeast, viral, eukaryotic or mammalian promoters, the selection of which depends on the host cell system used for expression.

By the term "regulatory element" is meant, for the purposes of the specification and claims to refer to control elements for efficient gene transcription or message translation including, but not limited to, enhancers, and transcription or translation initiation and termination signals. Enhancer sequences are DNA elements that appear to increase transcriptional efficiency in a manner relatively independent of their position and orientation with respect to a nearby gene. Thus, depending on the host cell expression vector system used, an enhancer may be placed either upstream or downstream from the inserted DNA molecule to increase transcriptional efficiency. Such regulatory elements may be inserted into nearby vector DNA sequences using recombinant DNA methods known in the art for insertion of DNA sequences.

By the term "vector" is meant, for the purposes of the specification and claims to refer to a DNA molecule capable of autonomous replication in a host cell, and which allow for cloning of DNA molecules. As known to those skilled in the art, a vector includes, but is not limited to, a plasmid, cosmid, phagemid, viral vectors, phage vectors, yeast vectors, mammalian vectors and the like.

In the preferred and illustrated embodiments, the vector according to the present invention comprises at least one promoter operably linked to a DNA sequence encoding an α-peptide; and one or more cloning sites cleavable by distinct restriction enzymes which have been introduced within the lacZ coding sequence from and including codon 8 and downstream of codon 8, in forming a modified lacZα coding sequence. Preferably, the modified lacZα coding sequence contains restriction enzyme sites in a region of the DNA sequence encoding the α-peptide, wherein the region corresponds to the DNA encoding amino acids 8 to 38 of β-galactosidase as shown in SEQ ID NO:1. Various bacterial, phage, or plasmid promoters known in the art from which a high level of transcription has been observed in a host cell system such as $E.\ coli$ include, but are not limited to, the lac promoter, trp promoter, tac promoter, recA promoter, ribosomal RNA promoter, the $P_R$ and $P_L$ promoters, T7 promoter, SP6 promoter, lacUV5, ompF, bla, and lpp. Various prokaryotic replicons are known to those skilled in the art, and function to direct autonomous replication and maintenance of a recombinant molecule, of which it is part of, in a prokaryotic host cell. The vector may further comprise selection means such as an antibiotic resistance gene, or a gene that complements an auxotroph. Various antibiotic resistance genes have been incorporated into vectors for the purpose of aiding selection of host cell clones containing such vectors. For example, antibiotic resistance genes incorporated into vectors intended for introduction into bacterial host cells include, but are not limited to, a gene that confers resistance to an antibiotic selected from the group consisting of ampicillin, kanamycin, tetracycline, neomycin, G418 and chloramphenicol. Genes for complementing an auxotroph are genes encoding enzymes or proteins which facilitate usage of nutritional or functional components by the host such as a purine, pyrimidine, amino acid (e.g., lysine, tryptophan, histidine, leucine, cysteine), or sphingolipid.

As appreciated by those skilled in the art, another embodiment of the vector according to the present invention includes at least one promoter operatively linked to a DNA sequence encoding an α-peptide; multiple cloning sites cleavable by distinct restriction enzymes which have been introduced within the lacZ coding sequence including codon 8 and downstream of codon 8, in forming a modified lacZα coding sequence; and a replicon that functions in eukaryotic cells. In one illustration of this embodiment, the modified lacZα coding sequence contains restriction enzyme sites in a region of the DNA sequence encoding the α-peptide, wherein the region corresponds to the DNA encoding amino acids 8 to 38 as shown in SEQ ID NO:1. Those skilled in the art will recognize that other regions downstream of amino acid 38 may be identified by using the methods described in the present invention. Various promoters for expression in eukaryotic cells are known in the art, including, but not limited to, viral or viral-like basal promoters like the SV40 late promoter, the RSV promoter, the CMV immediate early promoter, and a VL30 promoter; and yeast or mammalian cellular promoters (See, e.g., Larsen et al., 1995, *Nucleic Acids Res.* 23:1223–1230; Donis et al., 1993, *BioTechniques* 15:786–787; Donda et al., 1993, *Mol. Cell. Endocrinol.*

90:R23–26; and Huper et al., 1992, *In Vitro Cell Dev. Biol.* 28A:730–734). Various replicons are known to those skilled in the art that function in eukaryotic cells to direct replication and maintenance of a recombinant molecule, of which it is part of, in a eukaryotic host cell. The vector may further comprise selection means such as the use of thymidine kinase gene, an antibiotic resistance gene, or a gene that complements an auxotroph. Various antibiotic resistance genes have been incorporated into vectors for the purpose of aiding selection of eukaryotic host cell clones containing such vectors. For example, antibiotic resistance genes incorporated into vectors intended for introduction into eukaryotic host cells include, but are not limited to, a gene that confers resistance to an antibiotic selected from the group consisting of neomycin, and blastocidin S. For the lacZα marker inactivation system to work in eukaryotic cells, it is important to note that the host cell must also be engineered to express a β-galactosidase molecule to be complemented by the α-peptide, or the remainder of the lacZ gene be included along with the lacZα coding sequence on the same vector. However, successful expression and detection of the prokaryotic enzyme β-galactosidase in eukaryotic cells has been described previously (see, e.g., Rocha et al., 1996, *Br. J. Cancer* 74:1216–22), including substrates and suppression of endogenous activity (see, e.g., Hendrikx et al., 1994, *Anal. Biochem.* 222:456–60; Young et al., 1993, *Anal. Biochem.* 215:24–30).

Additionally, the vector according to the present invention may be sold in kit form. The kit comprises as a component the vector in sufficient amounts to perform multiple cloning reactions, and further comprises a component selected from the group consisting of host cells into which the recombinant vector is introduced, a chromogenic substrate (e.g., X-gal or MacConkey agar), an inducer of lacZα gene expression (e.g., IPTG), and one or more restriction enzymes specific for restriction enzyme sites within the modified lacZα coding sequence, and combinations thereof.

EXAMPLE 1

Illustrated in this example are methods and compositions for construction of one embodiment of a plasmid vector according to the present invention. The starting plasmid selected for vector construction was plasmid pBluescript II KS(−) (Short et al., 1988, supra; Alting-Mees and Short, 1989, supra). The initial step in construction involved removal of the 173-base pair multiple cloning sites from pBluescript II KS(−) to generate a progenitor plasmid for use in subsequent manipulations. This was accomplished by cleavage of pBluescript II KS(−) with BssHII and religation at low DNA concentration (5 ng/μl) to generate the plasmid pSNS416 which contains, sequentially, the ampicillin resistance gene, the colE1 origin of plasmid replication and an out of frame lacZα gene fragment (promoter/operator and first 60 codons of lacZ with a 10-base substitution for codon 6) followed, in the opposite orientation, by the f1 origin of replication which, in this configuration, allows for packaging of the antisense strand of lacZα into phage particles upon co-infection with a helper phage such as M13KO7 (Vieira and Messing, 1987, *Methods Enzymol.* 153:3–11).

To address the problem of unreliability of the color selection mechanism in the currently used vectors, a modified lacZα gene fragment was constructed in which restriction sites recognized by various restriction enzymes were introduced along the entire length of the coding sequence of lacZα. This construction, having multiple restriction enzyme sites, allowed investigation of the mechanism of color selection as a function of not only α-peptide expression, but also of α-peptide complementation function. The strategy illustrated in this embodiment for engineering these modifications into lacZα involved saturation of the wild type coding sequence with restriction enzyme sites by introducing base pair changes which resulted in creating the desired restriction enzyme sites but did not affect the coding specificity of the DNA (e.g., utilizing codon and third base degeneracy). However, using the methods according to the present invention and thus encompassed within the scope of the present invention, base pair changes may be made which affect the coding specificity of the wild type lacZα DNA and which result in either conservative or nonconservative amino acid substitutions that do not affect α-peptide complementation function in vivo.

Computer aided designs for implementation of this strategy were generated by employing a commercially available computer software. Initially, the proximal 60 amino acids of β-galactosidase, as specified by the shortest lacZ gene fragment known to be sufficient for providing α-complementation function (Yanisch-Perron et al., 1985, supra), were back translated into an ambiguous DNA sequence using the software's back translation function (see, e.g., FIG. 1). SEQ ID NO:1 shows the first 60 amino acids of β-galactosidase for which an ambiguous DNA sequence was computer generated. Next, using ambiguous DNA sequences, a listing was generated of all possible restriction sites useful for cloning which may be introduced into a DNA sequence encoding the amino acid sequence of SEQ ID NO:1 without affecting the amino acid sequence of SEQ ID NO:1. Since most cloning experiments require specific DNA termini, and since the restriction enzymes most useful for generating such termini in vectors are those that recognize six-base uninterrupted palindromes, preferred restriction enzyme sites for the vectors according to the present invention are those that recognize six-base uninterrupted palindromes. Of the 64 theoretically possible six-base palindromes, greater than 30 restriction enzyme sites recognized by known restriction enzymes were identified in DNA sequences encoding the amino acid sequence of SEQ ID NO:1, as shown in the example in FIG. 1. It is appreciated by those skilled in the art that such restriction enzyme sites may be other than six-base uninterrupted palindromes. For example, procedures similar to this can be performed for eight-base palindromes or other groups of restriction enzyme sites, depending on the desired cloning applications.

FIG. 1 illustrates the results of the design strategy showing some of the possible restriction enzyme sites introducible into the lacZα coding sequence. Note, however, that FIG. 1 is presented for purposes of illustration, and not limitation. For example, it is appreciated by those skilled in the art that other restriction sites may be created by means including introduction of codons in the region (codons 8 to 38) of the lacZα coding sequence which encode conservative amino acid substitutions such as Leu for Ile, Ala for Val, Ser for Thr and vice versa; or which encode nonconservative substitutions by screening for α-peptide complementation activity from a randomly generated library of sequences (see, e.g., Dunn et al., 1988, supra). Several criteria were used to choose which restriction enzyme sites to introduce along the entire length of the coding sequence of lacZα. These criteria included commercial availability of the respective restriction enzyme at the time the work was performed, occurrence in the vector, and spacing and nature and compatibility of the termini. Based on these criteria, a subset of 13 restriction enzyme sites were selected for engineering into the region of the coding sequence of lacZα. These 13 restriction enzyme sites, together with the recognition sequence for EspI, were introduced into lacZα by site-directed mutagenesis using the mutagenic oligonucleotides NV1P (SEQ ID NO:2) and NV2P (SEQ ID NO:3) to generate the plasmid pSNS448.

More specifically, pSNS416 was subjected to site-directed mutagenesis using a closing oligonucleotide method described previously (Slilaty et al., 1990, *Anal. Biochem.* 185:194–200) and mutagenic oligonucleotide NV1P (SEQ ID NO:2) to generate the plasmid pSNS432. Briefly, 0.1 pmol of pSNS416 template DNA was mixed with 2 pmol of closing oligonucleotide and 10 pmol of NV1P, in a final volume of 22 μl. To this mixture was added 3 μl of annealing buffer (200 mM Tris-HCl, pH 7.4, 20 mM MgCl$_2$, and 500 mM NaCl), and then incubated in a boiling water bath for 3 minutes. The mixture was then incubated on ice for 2 to 8 minutes, followed by the addition of 3 μl of DNA synthesis buffer (300 mM Tris-HCl, pH 7.8, 80 mM MgCl$_2$, 100 mM DTT, 10 mM ATP, 5 mM of each of dGTP, dATP, dCTP, and dTTP, and 500 μg/ml bovine serum albumin), 1 μl of T4 DNA ligase (1 unit/μl), and 1 μl of Klenow polymerase (7 units/μl), with subsequent incubation on ice for an additional 30 minutes. The reactions were then sequentially incubated at room temperature for 30 minutes, and 37° C. for 60 minutes. The reactions may then be used to transform competent cells, with subsequent screening for the desired construction. The resultant plasmid, pSNS432, comprised restoration of the lacZα reading frame and creation of sites for the restriction enzymes BclI, EspI, PstI, NruI, SmaI/XmaI, PvuII, ClaI, and FspI by the introduction of base changes that do not affect the original coding capacity of the DNA.

The coding sequence of lacZα in pSNS432 was further modified by a subsequent site-directed mutagenesis experiment using methods as described above and the mutagenic oligonucleotide NV2P (SEQ ID NO:3) to generate the plasmid pSNS448. The silent nucleotide substitutions introduced into the coding sequence of lacZα by NV2P created restriction sites for restriction enzymes NheI, EcoRI, BssHI, StuI, BglII, and DraI. Thus, pSNS448 contains sites for the restriction enzymes BclI, EspI, PstI, NruI, SmaI, PvuII, ClaI, FspI, RheI, EcoRI, BssHI, StuI, BglII, and DraI at codons 4, 8, 11, 15, 20, 24, 27, 30, 36, 39, 44, 47, 54, and 55 of lacZα, respectively. Accordingly, one embodiment of a plasmid vector according to the present invention is illustrated by pSNS448. More specifically, one embodiment of a plasmid according to the present invention comprises a base plasmid vector having a coding sequence of lacZα having multiple cloning sites contained in the region corresponding to codons 8 through 38 of lacZ, as illustrated in FIG. 2, which corresponds to nucleotide position 112 to nucleotide position 204 of SEQ ID NO:7. Additionally, the modified lacZα coding sequence of pSNS448 may be used as the progenitor for embodiments of other vectors according to the present invention, by using standard molecular biologic techniques, including for the vector embodiments pTrueBlue™ and M13TrueBlue™.

It will be recognized by those skilled in the art that the method of the present invention can be readily applied to genes or gene fragments other than lacZ or lacZα to generate color indicator cloning vectors (e.g. a GFP-based vector, Cubitt et al., 1995, supra; herein incorporated by reference) or positive selection cloning vectors (e.g. ccdB-based vector, Bernard et al., 1994, supra, herein incorporated by reference, or a GATA-1-based vector, Trudel et al., 1996, supra, herein incorporated by reference), having characteristics and accuracy similar to those of the lacZα-based vectors described herein.

EXAMPLE 2

Illustrated in this example are methods and compositions for construction of another embodiment of a plasmid vector according to the present invention. pSNS448, containing a modified lacZα coding sequence, was further modified in regions upstream and downstream of the coding sequence of lacZα using the closing oligonucleotide method described above, and mutagenic oligonucleotides. The further modifications were designed to add other features useful for protein expression and other molecular manipulations. One or more of the further modifications may be used to achieve a plasmid vector according to the present invention. For example, to sequences 5' of the lacZα coding sequence in pSNS448, the mutagenic oligonucleotide NV5'P (SEQ ID NO:4) was used to create the plasmid pSNS457 by looping-in sequences for an optimized ribosomal binding region (Gold and Stormo, 1990, *Methods Enzymol.* 185:89–90; see nucleotide positions 35 to 46 of SEQ ID NO:7); the restriction endonucleases NcoI and a SalI (see nucleotide positions 47 to 52, and 52 to 57, respectively of SEQ ID NO:7); a phage promoter (e.g., T7 promoter; Schenborn and Mierendorf, 1985, *Nucl. Acids Res.* 13:6223–6236; see nucleotide positions 55 to 76 of SEQ ID NO:7); and restriction enzymes SfiI, ApaI/Bsp120I, KpnI/Acc65I, BamHI and XhoI (see nucleotide positions 77 to 89, 85 to 90, 91 to 96, 98 to 103, and 103 to 108, respectively of SEQ ID NO:7). The resultant plasmid, pSNS457, is another embodiment of the plasmid vector according to the present invention.

Figure 2B:
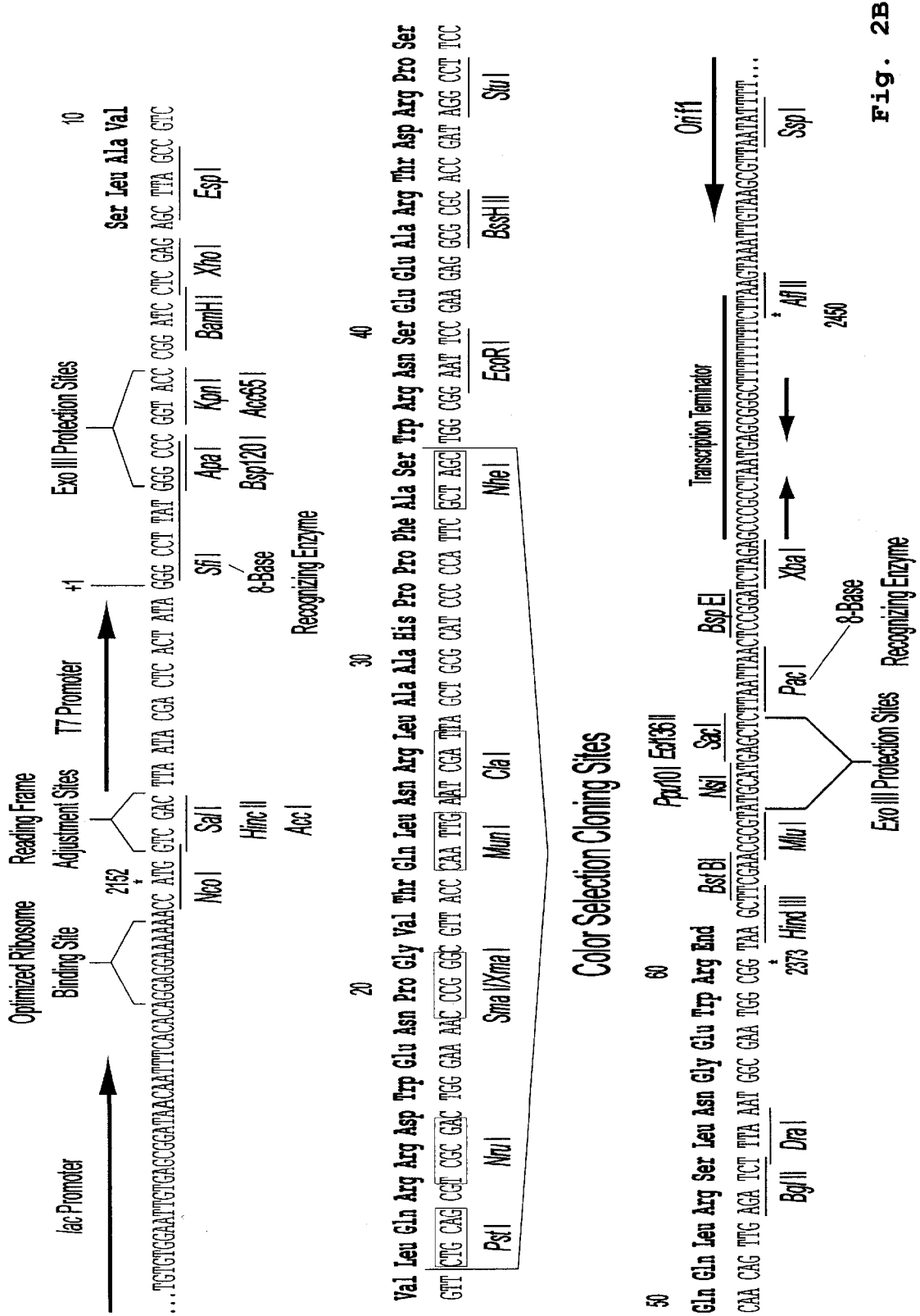
FIG. 2B is an enlarged view of a region contained within the plasmid construct shown in FIG. 2A, illustrating multiple cloning sites within a region of the lacZα coding sequence (see bracket labeled "Color Selection Cloning Sites" and various other features; This sequence is disclosed as SEQ ID NO:7).

Additional modifications may be made in sequence 3' to the lacZα coding sequence. For example, mutagenic oligonucleotides such as those illustrated in SEQ ID NO:5 and SEQ ID NO:6 may be used sequentially with plasmid pSNS457 to generate the plasmid pSNS524 by adding restriction sites for the restriction enzymes HindIII, BstBI, MluI, NsiI/Ppu10I, SacI/Ecl136II, PacI, BspEI and XbaI; the rho-independent trpA transcription terminator (Christie et al., 1981, *Proc. Natl. Acad. Sci. USA* 78:4180); and an AflII site (as illustrated in FIG. 2B). The plasmid pSNS524 is another embodiment of the plasmid vector according to the present invention. In making the different embodiments, of the plasmid vector according to the present invention, it may be desirable to substitute one restriction enzyme site for another or introduce new ones. For example, the PvuII site (CAGCTG) between SmaI site and the ClaI site (see Example 1) in pSNS524 may be converted to a MunI site (CAATTG) using adapter insertion or other methodology known to those skilled in the art to generate the plasmid pSNS527, referred to herein as pTrueBlue™ and illustrated in FIGS. 2A and 2B. Additionally, in another embodiment a phage promoter different than or the same as that located in the sequences 5' of the lacZα coding sequence, and in opposite orientation to that of the lac promoter (e.g., SP6 promoter; Schenborn and Mierendorf, 1985, supra) may also be added to the sequences 3' of the lacZα coding sequence.

In making the different embodiments of the plasmid according to the present invention, it may be desirable to confirm the intended modifications by DNA sequencing of both strands of the modified region using the dideoxy chain termination method or other standard method of DNA sequencing known in the art. In summary of Examples 1 and 2, one embodiment of the plasmid according to the present invention comprises at least one promoter (e.g., lac promoter, or other promoter depending on the host cell system) operatively linked to a DNA sequence encoding an α-peptide; multiple cloning sites consisting of restriction sites, cleavable by distinct restriction enzymes, which have been introduced into and are contained within a region of the DNA sequence encoding the α-peptide, wherein the region corresponds to the DNA encoding amino acids 8 to 38 as shown in SEQ ID NO:1; and a replicon. The plasmid vector according to the present invention may further comprise at least one additional feature, located outside the lacZα encoding sequence, selected from the group consisting of an antibiotic resistance gene, a ribosomal binding region, a transcription terminator (for stable clones and high-level protein expression, see, e.g., nucleotide positions 335 to 365 of SEQ ID NO:7), at least one phage promoter (for preparation of RNA probes in vitro); one or more restriction sites comprising an eight-base recognition sequence (e.g. for mapping and manipulation of large inserts); at least one restriction site for an endonuclease that generates ExoIII resistant 3' overhangs (for creating unidirectional deletions; see, e.g., nucleotide positions 287 to 298 of SEQ ID NO:7), a phage origin of replication (e.g., f1, Short et al., 1988, supra; Alting-Mees and Short, 1989, supra; see, e.g., FIG. 2) inserted in the opposite orientation to that of lacZα coding sequence (thereby facilitating the design of mutagenic, sequencing and other oligonucleotides by allowing recovery of the antisense strand), and combinations thereof.

EXAMPLE 3

Illustrated in this example are methods and compositions for construction of one embodiment of a phage vector according to the present invention. The phage vector according to the present invention contains one or more cloning sites consisting of restriction sites cleavable by distinct restriction enzymes within a region of the DNA sequence encoding the α-peptide, wherein the region containing the sites corresponds to the DNA encoding amino acids 8 to 38 as shown in SEQ ID NO:1. An M13 phage version, containing a lacZα coding sequence, was constructed by replacing the original promoter-lacZα coding sequences comprising 548 base pairs between PvuII and Bsu36I in M13mp19 (Yanish-Perron et al., 1985, supra) with the modified lacZα coding sequences (268 base pairs) from pSNS448 described above. In one illustration of this method, an AseI-BglII restriction fragment (from just upstream of the lac promoter to about codon 54) was removed from pSNS448. This fragment and the M13mp19 restricted with PvuII and Bsu36I were filled-in to form blunt ends using the standard methods known to those skilled in the art, and using Klenow fragment of DNA Polymerase I in a buffer containing all four nucleotides. Following the fill-in reactions, the fragment and restricted M13mp19 were blunt-end ligated. One of the resultant phage isolates, which was designated M13sp3, contained the modified lacZα fragment (modified with the multiple restriction enzyme sites in accordance with the present invention) in the same orientation as the original lacZα in M13mp19. Phage Ml3sp3 is one embodiment of the phage vector according to the present invention.

Figure 3A:
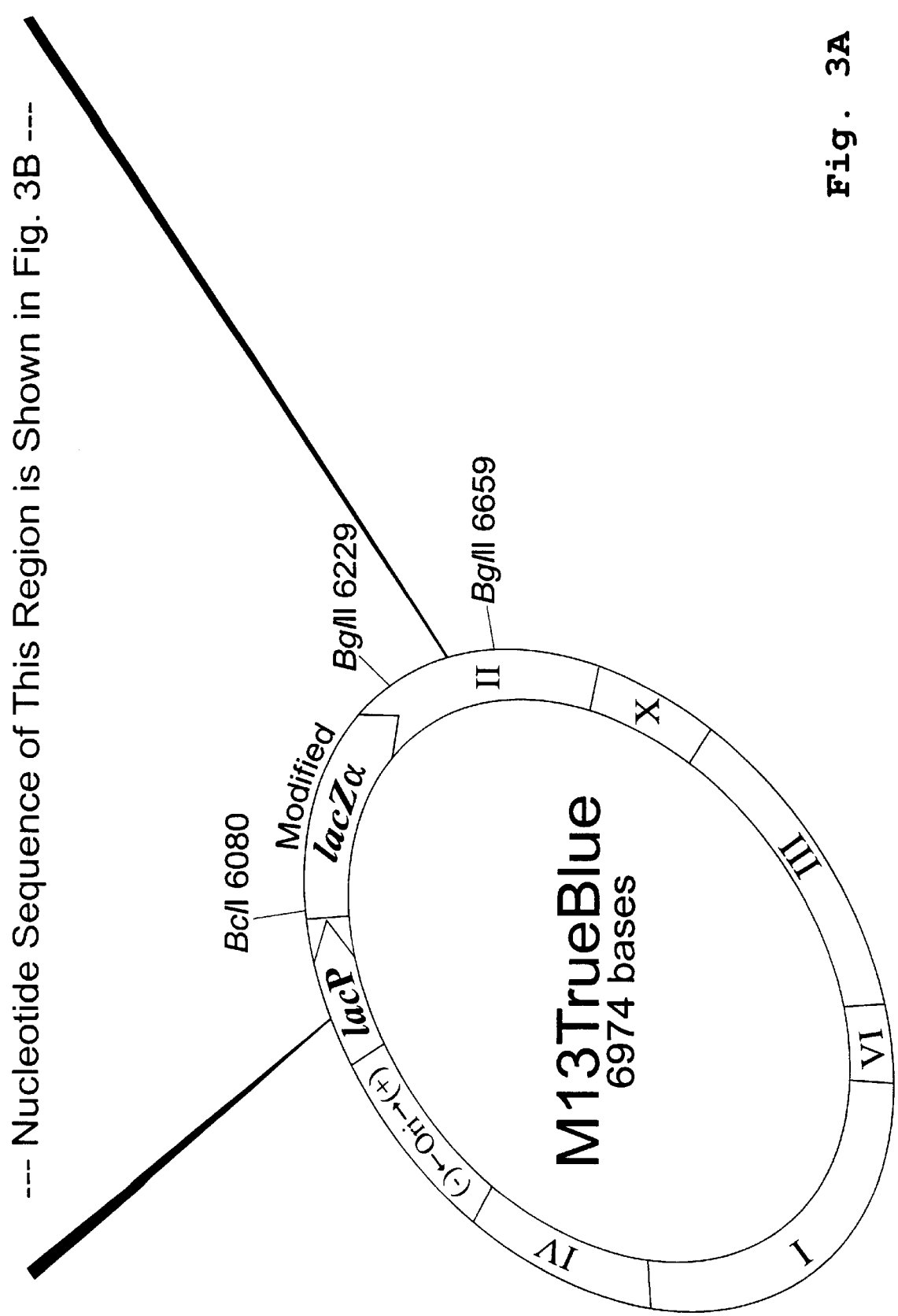
FIG. 3A is a schematic illustration of an embodiment of a phage construct according to the present invention.

Phage M13sp3 was used as a template for further modifications by subsequent site-directed mutagenesis. In one modification reaction using the methods as described above, a mutagenic oligonucleotide (SEQ ID NO:8) was used to destroy the first of two ClaI sites within the M13 genome at position 2,527 of the conventional M13mp19 map (Yanish-Perron et al., 1985, supra). The resultant phage, M13sp5, is another embodiment of the phage vector according to the present invention. Phage M13sp5 was used as a template in a further site-directed mutagenesis reaction employing a mutagenic oligonucleotide (SEQ ID NO:9) to destroy the second ClaI site at position 6,882 of M13mp19 in generating the phage M13sp7. In making the different embodiments, of the plasmid vector according to the present invention, it may be desirable to substitute one restriction enzyme site for another or introduce new ones. For example, the PvuII site (CAGCTG) between SmaI site and the ClaI site (see Example 1) in M13sp7 may be converted to a MunI site (CAATTG) using adapter insertion or other methodology known to those skilled in the art to generate the M13sp13. M13sp13 is another embodiment of the phage vector according to the present invention, a schematic map of which is illustrated as M13TrueBlue in FIGS. 3A and 3B, and relevant sequence (lac promoter and modified lacZα coding sequence) of which is shown in SEQ ID NO:10.

Although it is possible to clone large DNA fragments in M13, large inserts are known to be unstable (see, e.g., Messing, 1983, supra; Yanisch-Perron et al., 1985, supra). It is noted that replacing a 548 base pair fragment containing lacZα coding sequences with the modified lacZα coding sequences (268 base pairs) results in a 280 base pair reduction in size of the vector. Thus, an additional advantage of the phage vector according to the present invention is that it would add to the stability of DNA inserts, as compared to the currently used M13 phage.

EXAMPLE 4

Figure 4A:
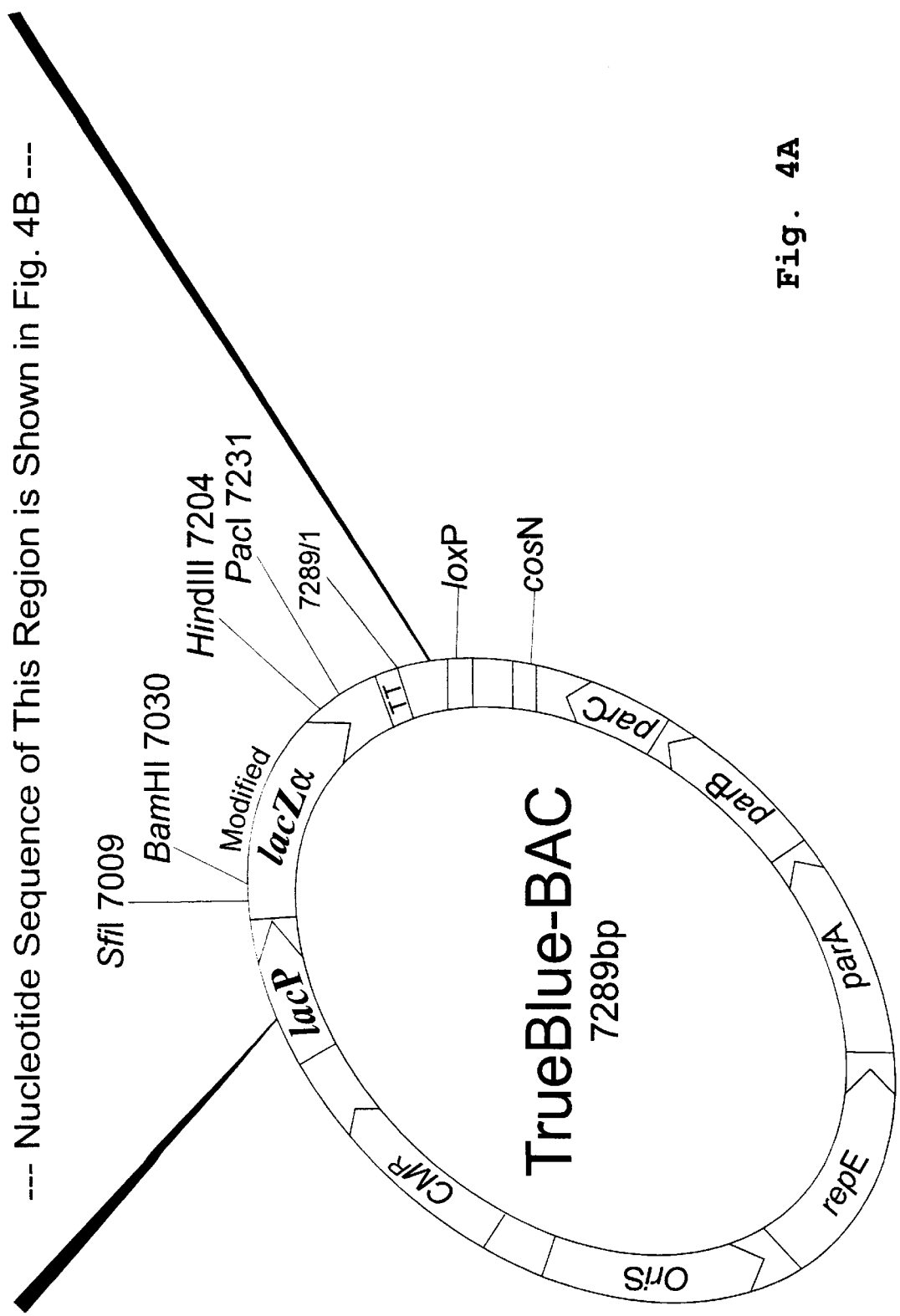
FIG. 4A is a schematic illustration of a bacterial artificial chromosome vector according to the present invention.
Figure 4B:
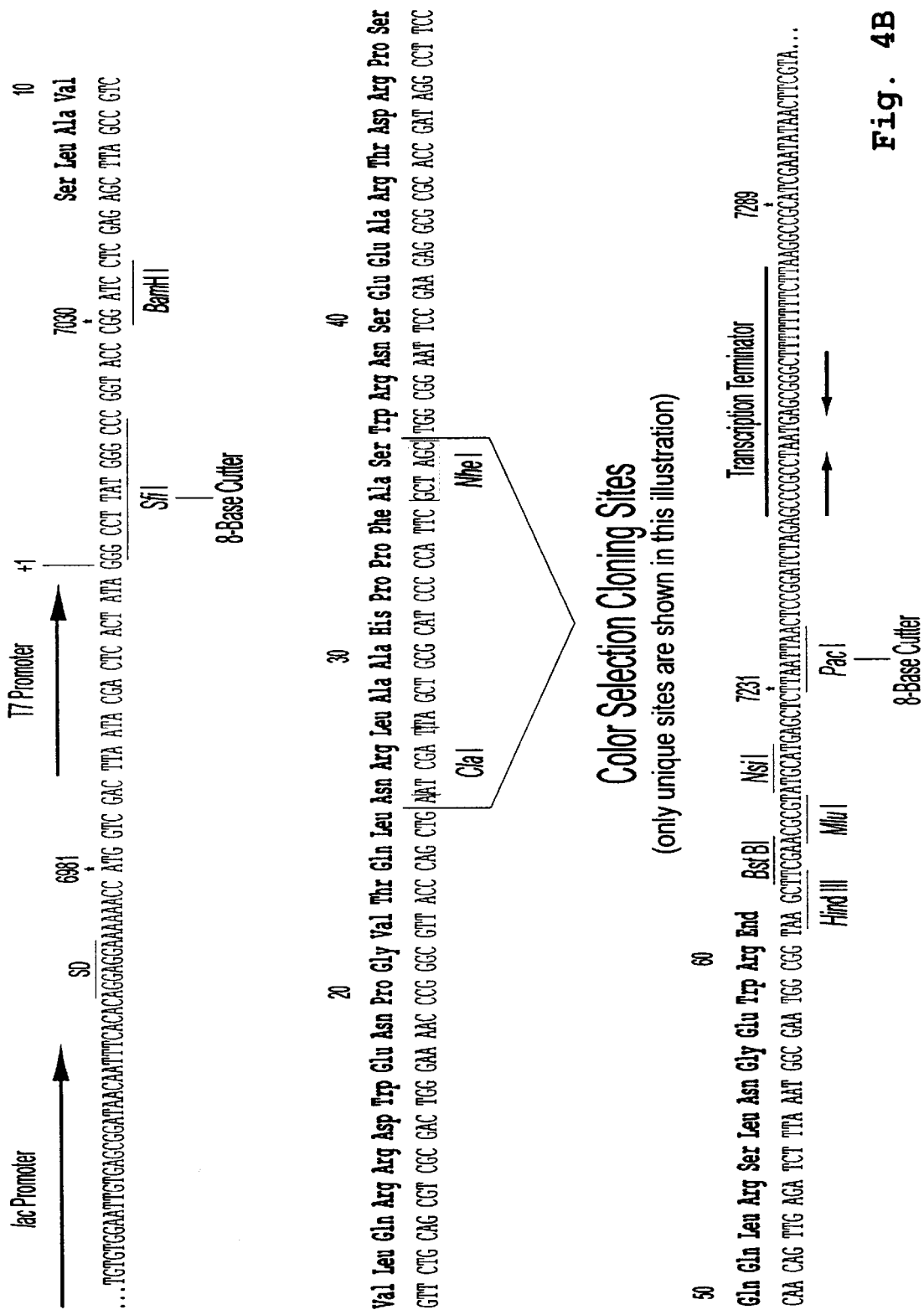
FIG. 4B is an enlarged view of a region contained within the bacterial artificial chromosome vector shown in FIG. 4A, illustrating multiple cloning sites within a region of the lacZα coding sequence (see bracket labeled "Color Selection Cloning Sites" and various other features; This sequence is disclosed as SEQ ID NO:11. The amino acid sequence is amino acids 6–61 of SEQ ID NO:1.

Illustrated in this example are methods and compositions for construction of one embodiment of a bacterial artificial chromosome vector according to the present invention. The bacterial artificial chromosome vector according to the present invention contains one or more cloning sites consisting of restriction sites cleavable by distinct restriction enzymes within a region of the DNA sequence encoding the α-peptide, wherein the region containing the sites corresponds to the DNA encoding amino acids 8 to 38 as shown in SEQ ID NO:1. A bacterial artificial chromosome embodiment of the present invention was constructed by replacing the original promoter-lacZα coding sequences comprising approximately 630 base pairs between NotI and SfiI in pBeloBAC11 (Shizuya et al., 1992, Proc. Natl. Acad. Sci USA 89:8794–8797) with the modified lacZα coding sequences from pSNS524 described above. In one illustration of this method, an approximately 423 base pair restriction fragment from AseI just upstream of the lac promoter to the AflII restriction site just downstream of the transcription terminator was removed from pSNS524. This fragment and the pBeloBAC11 DNA restricted with NotI and SfiI were filled-in to form blunt ends using the standard methods known to those skilled in the art, and using the Klenow fragment of DNA polymerase I in a buffer containing all four nucleotides. Following the fill-in reactions, the fragment and restricted pBeloBAC11 were blunt-end ligated. One of the resultant isolates, which was designated pSNSS28, contained the modified lacZα fragment (modified with the multiple restriction enzyme sites in accordance with the present invention) in the same orientation as original lacZα in pBeloBAC11. The plasmid, pSNS528, is one embodiment of the bacterial artificial chromosome vector according to the present invention and is illustrated as TrueBlue-BAC™ in FIGS. 4A and 4B, and relevant sequence (lac promoter and modified lacZα coding sequence) of which is shown in SEQ ID NO:11.

EXAMPLE 5

Illustrated in this example is the efficiency of color selection using the modified lacZα gene fragment (coding sequence) according to the present invention, and methods and compositions for testing the same. In one method for evaluating the efficiency of color selection in the modified lacZα gene fragment, a two to four base pair insertion or deletion was created at each of the newly engineered restriction sites in the modified lacZα coding sequence. This was accomplished by cleavage of pSNS448 DNA, described above and representing the modified lacZα coding sequence found in the vectors according to the present invention, with different restriction enzymes followed by filling-in or recessing the DNA overhangs by treatment with the Klenow enzyme and religation of the blunt termini. These manipulations resulted in the formation of lacZα mutants in which the reading frame had been shifted at the site of restriction enzyme cleavage. Shifting the reading frame is what would be expected by the insertion of a DNA molecule at that restriction enzyme site. Transformation of the DNA molecules produced in this fashion into an indicator host strain of E. coli yielded both white and blue colonies. The proportion of white colonies observed for each restriction site is an indication of the importance of the coding sequence upstream of that site in producing a functional α-peptide. It is noted that using this method of analysis, some blue colonies will always result due to incomplete reactions at the restriction digestion and fill-in/recession steps. In fact, control reactions in which ligase was omitted yielded essentially 100% blue colonies (e.g., unrestricted vector). The results of this analysis, shown in Table 1, delineate a region where interruption of the lacZα coding sequence leads to the formation of a non-functional α-peptide. As shown in Table 1, this region includes the EspI site at codon 8 to the EcoRI site at codon 39, and does not include the sequences upstream of codon 7 of the lacZα coding sequence which are used by the currently available lacZα vectors for the cloning of DNA inserts. Filling-in of the BssHII site at codon 44 resulted in only 3% white colonies, indicating the end of the region of the lacZα coding sequence that is essential for producing a functional α-peptide (see also FIG. 2B). Also shown in Table 1 is the number of readthrough amino acids resulting from the shift in the reading frame.

TABLE 1

| Restriction enzyme | lacZα codon | Read-through | # Blue colonies | # white colonies | % white colonies |
| --- | --- | --- | --- | --- | --- |
| EspI | 8 | n.a. | 531 | 42 | 7 |
| PstI | 11 | 12 | 102 | 123 | 55 |
| XmaI | 20 | 16 | 776 | 819 | 51 |
| ClaI | 27 | 1 | 124 | 470 | 79 |
| NheI | 36 | 0 | 164 | 767 | 82 |
| EcoRI | 39 | 0 | 104 | 475 | 82 |
| BssHII | 44 | 3 | 234 | 8 | 3 |
| BglII | 54 | 12 | 448 | 283 | 39 | n.a.—denotes "not applicable", as reading frame shift did not result.

A second method, used to investigate the mechanism of color selection in the modified lacZα coding sequence, involved insertion of a DNA molecule into each of the newly created restriction enzyme sites. Random fragments of λ phage DNA were shotgunned into the various newly introduced restriction sites in lacZα and the resultant colonies or plaques were sampled and analyzed for the presence or absence of DNA molecule inserts. Bacteriophage λ DNA was digested with PstI, MspI, ApoI, BssHII or BstYI and the resulting fragments were cloned by shotgun ligation into pSNS448 DNA or functionally equivalent plasmid, described above and representing the modified lacZα coding sequence found in the vectors according to the present invention, which had been linearized by cleavage with PstI, ClaI, EcoRI, BssHII, or BglII or BamHI, respectively. For pSNS448 DNA or functionally equivalent plasmid linearized with the blunt-end cutting enzymes NruI, SmaI and StuI, or blunted by fill-in as described above for the NheI and EspI sites, λ DNA digested with HaeIII was used. Similarly, λ DNA digested with HaeIII was used to perform random insertions into M13TrueBlue™ replicative form DNA which had been linearized by cleavage with SmaI or FspI. When M13TrueBlue™ DNA had been linearized with ClaI, λ DNA digested with MspI was employed. Following transformation of E. coli host strain HB2151 and plating of cells onto media containing X-gal and IPTG, blue colonies and blue plaques were grown and the plasmid DNA or replicative form M13 phage DNA was isolated and screened for carrying an insert within the modified lacZα gene fragment by cleavage with BamHI plus HindIII for plasmid DNA, and AvaI plus EcoRI for M13 phage DNA.

Since false negatives (blue colonies or blue plaques harboring vectors with DNA inserts) are far more problematic than false positives in terms of their contribution to errors in screening for recombinant clones, analysis of lacZα insertional inactivation was focused almost entirely on understanding the structure of the plasmid carried by blue colonies or M13 phage DNA carried by blue plaques. Table 2 shows the results of analysis of the plasmid isolated from blue colonies for the presence of DNA molecule inserts, and Table 3 shows the results of analysis of the M13 phage DNA isolated blue plaques for the presence of DNA molecule inserts. It is evident from these results that blue colonies and blue plaques correctly reflect the structure of the respective vector they are carrying only when insertion of a DNA molecule took place within the codons encoding the structurally essential elements of the α-peptide (i.e., codons 8 to 38). When insertion of the DNA molecule was attempted upstream or downstream of this essential region, false negatives arose at high frequencies (see, e.g., Table 2).

TABLE 2

Analysis of insertions into lacZα in plasmid DNA of blue colonies

| restriction enzyme | lacZα codon | # insert positive | # insert negative | % insert negative |
| --- | --- | --- | --- | --- |
| BclI/BamHI | 4 | 16 | 22 | 58% |
| EspI | 8 | 4 | 11 | 73% |
| PstI | 11 | 0 | 15 | 100% |
| NruI | 15 | 0 | 12 | 100% |
| SmaI | 20 | 0 | 15 | 100% |
| ClaI | 27 | 1* | 54 | 98% |
| FspI | 30 | n.d. | n.d. | n.a. |
| NheI | 36 | 0 | 32 | 100% |
| EcoRI | 39 | 12 | 15 | 56% |
| BssHII | 44 | n.d. | n.d. | n.a. |
| StuI | 47 | 7 | 2 | 22% |
| BglII | 54 | 6 | 3 | 33% |

*plasmid dimer anomaly;
n.d.—not determined;
n.a.—not applicable

TABLE 3

Analysis of insertions into lacZα in M13 phage DNA of blue plaques

| restriction enzyme | lacZα codon | # insert positive | # insert negative | % insert negative |
| --- | --- | --- | --- | --- |
| EspI | 8 | n.d. | n.d. | n.a. |
| PstI | 11 | n.d. | n.d. | n.a. |
| NruI | 15 | n.d. | n.d. | n.a. |
| SmaI | 20 | 0 | 48 | 100% |

TABLE 3-continued

Analysis of insertions into lacZα in M13 phage DNA of blue plaques

| restriction enzyme | lacZα codon | # insert positive | # insert negative | % insert negative |
|---|---|---|---|---|
| ClaI | 27 | 0 | 43 | 100% |
| FspI | 30 | 0 | 34 | 100% |
| NheI | 36 | n.d. | n.d. | n.a. |
| EcoRI | 39 | n.d. | n.d. | n.a. |
| BssHII | 44 | n.d. | n.d. | n.a. |
| StuI | 47 | n.d. | n.d. | n.a. |
| BglII | 54 | n.d. | n.d. | n.a. | n.d.—not determined;
n.a.—not applicable

In summary, the results of the fill-in/recession studies outlined in Table 1, and the insertional inactivation experiments detailed in Tables 2 and 3, collectively define a region of the lacZα coding sequence where reliable color selection as well as virtual absence of false negatives can be achieved. This region extends from the EspI site at codon 8 through the NheI site at codon 36, and to codon 38. The result obtained for the next restriction site, EcoRI at codon 39, were mixed. While the fill-in data suggest that this site is essential for α-peptide function (see Table 1), the insertional inactivation data suggest otherwise (see Table 2). It is possible therefore, that the region of accuracy extends through the EcoRI site at codon 39 down to codon 43 just upstream of the BssHII site at codon 44 where the end of the essential region of the α-peptide is clearly marked by the concurrence of both types of data (see Tables 1 and 2). One of the most important characteristics of this region of lacZα coding sequence is its ability to virtually eliminate the generation of false negatives. In fact, out of a total of 308 blue colonies or blue plaques resulting from cloning experiments performed in this region, only one was found to carry an insert (along with a second intact copy of the lacZα gene fragment, e.g., the plasmid dimer anomaly denoted in Table 2). This region of the lacZα coding sequence therefore, together with the 10 illustrated restriction enzyme sites, EspI, PstI, NruI, SmaI/XmaI, PvuII/MunI, ClaI, FspI and NheI, provides a first opportunity for performing color selection cloning where the probability of false negative events is at virtual zero. This is particularly important for development of ordered genomic libraries and shotgun DNA sequencing procedures where blue colonies or blue plaques which could contain DNA fragments essential for formation of a complete "contig" are not analyzed.

EXAMPLE 6

Illustrated in this embodiment are methods for using a vector according to the present invention, wherein the method comprises using at least one restriction enzyme site, within a modified lacZα coding sequence, to clone a DNA molecule. One illustration of the method of using a vector according to the present invention, wherein the vector comprises a marker inactivation system utilizing a modified lacZα coding sequence, comprises cloning (directionally or nondirectionally) a DNA molecule into a single restriction enzyme site in the region of the modified lacZα coding sequence, corresponding to DNA sequence encoding amino acids 8 to 38 of β-galactosidase as illustrated in SEQ ID NO:1, in forming recombinant vectors. For example, the DNA molecule may have ClaI compatible ends, and then be cloned into the ClaI site in the modified lacZα coding sequence; followed by introducing the resultant recombinant vectors into competent host cells; growing the host cells in the presence of a chromogenic substrate cleavable by β-galactosidase; and screening for indicia of lac operon marker inactivation selected from the group consisting of white colonies (if a plasmid or a bacterial artificial chromosome vector is used), clear plaques (if a phage vector is used), and lack of cell-staining (if a vector for eukaryotic cells is used). The method may further comprise adding an inducer of lacZα gene expression when the host cells are grown in the presence of a chromogenic indicator for β-galactosidase activity such as x-gal or MacConkey agar.

Another illustration of the method of using a vector according to the present invention, wherein the vector comprises a marker inactivation system utilizing a modified lacZα coding sequence, comprises cloning (directionally or nondirectionally) of a DNA molecule into two restriction enzyme sites in a region of the modified lacZα coding sequence, corresponding to DNA sequence encoding amino acids 8 to 38 of β-galactosidase as illustrated in SEQ ID NO:1, in forming recombinant vectors. For example, the DNA molecule may have a PstI compatible end and an NheI compatible end, and then be cloned into the modified lacZα coding sequence which had been restricted with PstI and ANeI; followed by introducing the resultant recombinant vectors into competent host cells; growing the host cells in the presence of a chromogenic substrate cleavable by β-galactosidase; and screening for indicia of lac operon marker inactivation selected from the group consisting of white colonies (if a plasmid or a bacterial artificial chromosome vector is used), clear plaques (if a phage vector is used), and lack of cell-staining (if a vector for eukaryotic cells is used). The method may further comprise adding an inducer of lacZα gene expression when the host cells are grown in the presence of a chromogenic substrate or indicator for β-galactosidase activity such as x-gal or MacConkey agar.

Another method of using a vector according to the present invention, wherein the vector comprises a marker inactivation system utilizing a modified lacZα coding sequence, comprises cloning (directionally or nondirectionally) of a DNA molecule into a restriction enzyme site in a region of the modified lacZα coding sequence, corresponding to DNA sequence encoding amino acids 8 to 38 of β-galactosidase as illustrated in SEQ ID NO:1, and a restriction enzyme site (either in the lacZ encoding sequence or vector sequence) which is upstream of such region of the modified lacZα coding sequence in forming recombinant vectors. For example, and with reference to FIG. 2B, the DNA molecule may have a BamHI compatible end and an XmaI compatible end, and then be cloned into a vector cleaved at a BamHI site upstream of the codon for amino acid 8, and cleaved at the XmaI site; followed by introducing the resultant recombinant vectors into competent host cells; growing the host cells in the presence of a chromogenic indicator for β-galactosidase activity; and screening for indicia of lac operon marker inactivation selected from the group consisting of white colonies (if a plasmid or a bacterial artificial chromosome vector is used), clear plaques (if a phage vector is used), and lack of cell-staining (if a vector for eukaryotic cells is used). The method may further comprise adding an inducer of lacZα gene expression when the host cells are grown in the presence of a chromogenic indicator for β-galactosidase activity.

A further method of using a vector according to the present invention, wherein the vector comprises a marker inactivation system utilizing a modified lacZα coding sequence, comprises cloning (directionally or nondirectionally) of a DNA molecule into a restriction enzyme site in a region of the modified lacZα coding sequence, corresponding to DNA sequence encoding amino acids 8 to 38 of β-galactosidase as illustrated in SEQ ID NO:1, and a restriction enzyme site (in the lacZ coding sequence or in the vector sequence) which is downstream of such region of the modified lacZα coding sequence in forming recombinant vectors. For example, and with reference to FIG. 2B, the DNA molecule may have a BglII compatible end and a NruI compatible end, and then be cloned into a vector cleaved at a BglII site downstream of the codon for amino acid 38, and cleaved at the NruI site in the region of codons 8 to 38 of the modified lacZα coding sequence; followed by introducing the resultant recombinant vectors into competent host cells; growing the host cells in the presence of a chromogenic substrate cleavable by β-galactosidase; and screening for indicia of lac operon marker inactivation selected from the group consisting of white colonies (if a plasmid vector is used), clear plaques (if a phage vector is used), and lack of cell-staining (if a vector for eukaryotic cells is used). The method may further comprise adding an inducer of lacZα gene expression when the host cells are grown in the presence of a chromogenic indicator for β-galactosidase activity.

An additional illustration of the method of using a vector according to the present invention, wherein the vector comprises a marker inactivation system utilizing a modified lacZα coding sequence, comprises cloning (directionally or nondirectionally) of a DNA molecule into a restriction enzyme site in the lacZ coding region or in the vector sequence which is upstream of a region of the modified lacZα coding sequence that corresponds to DNA sequence encoding amino acids 8 to 38 of β-galactosidase as illustrated in SEQ ID NO:1, and a restriction enzyme site downstream of such region but still within the modified lacZα coding sequence, in forming recombinant vectors. For example, and with reference to FIG. 3B, the DNA molecule may have a BclI compatible end and a StuI compatible end, and then be cloned into a vector cleaved at a BclII site upstream of the codon for amino acid 8, and cleaved at the StuI site downstream of the region between codon 8 and 38 but still at a restriction site engineered into the sequence of the modified lacZα coding sequence; followed by introducing the resultant recombinant vectors into competent host cells; growing the host cells in the presence of a chromogenic indicator for β-galactosidase activity; and screening for indicia of lac operon marker inactivation selected from the group consisting of white colonies (if a plasmid vector is used), clear plaques (if a phage vector is used), and lack of cell-staining (if a vector for eukaryotic cells is used). The method may further comprise adding an inducer of lacZα gene expression when the host cells are grown in the presence of a chromogenic indicator for β-galactosidase activity.

From the foregoing, it will be obvious to those skilled in the art that various modifications in the above-described methods, and vector constructs can be made without departing from the spirit and scope of the invention. Accordingly, the invention may be embodied in other specific forms without departing from the spirit or essential characteristics thereof. Present embodiments and examples, therefore, are to be considered in all respects as illustrative and not restrictive, and all changes which come within the meaning and range of equivalency of the claims are therefore intended to be embraced therein.

What is claimed is:

1. A vector for cloning a DNA molecule, wherein the vector comprises at least one promoter operably linked to a modified *Escherichia coli* lacZ coding sequence encoding an α-peptide and containing at least one cloning site cleavable by a restriction enzyme wherein the modified lacZ coding sequence is made by introducing at least one cloning site within a lacZ coding sequence downstream of and including the codon corresponding to the codon designated as codon 8 in the native *E. coli* lacZ coding sequence.

2. The vector according to claim 1, wherein the at least one cloning site is introduced within a lacZ coding sequence from and including the codon for amino acid 8 to and including the codon for amino acid 38 of β-galactosidase.

3. The vector according to claim 1, wherein the at least one cloning site is a six-base palindrome.

4. The vector according to claim 1, wherein the at least one cloning site is a restriction site selected from the group consisting of sites cleaved by the enzymes EspI, PstI, NruI, SmaI/XmaI, PvuII, MunI, ClaI, AgeI, FspI and NheI.

5. The vector according to claim 2, wherein the at least one cloning site is a six-base palindrome.

6. The vector according to claim 2, wherein the at least one cloning site is a restriction site selected from the group consisting of sites cleaved by the enzymes EspI, PstI, NruI, SmaI/XmaI, PvuII, MunI, ClaI, AgeI, FspI and NheI.

7. The vector according to claim 1, wherein the vector is a plasmid vector.

8. The plasmid vector according to claim 7, wherein the plasmid vector is pSNS527.

9. The vector according to claim 1, wherein the vector is a bacterial artificial chromosome vector.

10. The bacterial artificial chromosome vector according to claim 9, wherein the bacterial artificial chromosome vector is pSNS528.

11. The plasmid vector according to claim 7, wherein the at least one cloning site is a six-base palindrome.

12. The plasmid vector according to claim 7, wherein the at least one cloning site is a restriction site selected from the group consisting of sites cleaved by the following restriction enzymes: EspI, PstI, NruI, SmaI/XmaI, MunI, ClaI, AgeI, FspI and NheI.

13. The plasmid vector according to claim 7, further comprising at least one additional feature, located outside the lacZ coding sequence, selected from the group consisting of a replicon, an antibiotic resistance gene, a gene that functionally complements an auxotroph, a ribosomal binding region, a transcription terminator, at least one phage promoter, one or more restriction sites comprising an eight-base recognition sequence, at least one restriction site for an endonuclease that generates ExoIII resistant 3' overhangs, a phage origin of replication, and combinations thereof.

14. The plasmid vector according to claim 13, wherein the antibiotic resistance gene is a gene that confers resistance to an antibiotic selected from the group consisting of ampicillin, kanamycin, tetracycline, and chloramphenicol.

15. The vector according to claim 1, wherein the vector is a phage vector.

16. The phage vector according to claim 15, wherein the phage vector is M13sp13.

17. The phage vector according to claim 15, wherein the at least one cloning site is a six-base palindrome.

18. The phage vector according to claim 15, wherein the at least one cloning site is a restriction sites selected from the group consisting of sites cleaved by the enzymes: EspI, PstI, KruI, SmaI/XmaI, PvuII, MunI, ClaI, AgeI, FspI, and RheI.

19. A kit comprising as a component the vector according to claim 1, and further comprises a component selected from the group consisting of host cells into which the vector is introduced, a chromogenic substrate or indicator for β-galactosidase activity, an inducer of lacZ gene expression, one or more restriction enzymes specific for restriction sites located within the vector, and combinations thereof.

20. A kit comprising as a component the vector according to claim 7, and further comprises a component selected from the group consisting of host cells into which the plasmid vector is introduced, a chromogenic substrate or indicator for β-galactosidase activity, an inducer of lacZ gene expression, one or more restriction enzymes specific for restriction sites located within the vector, and combinations thereof.

21. A kit comprising as a component the vector according to claim 15, and further comprises a component selected from the group consisting of host cells into which the phage vector is introduced, a chromogenic substrate or indicator for β-galactosidase activity, an inducer of lacZ gene expression, one or more restriction enzymes specific for restriction sites located within the vector, and combinations thereof.

22. A method of using the vector according to claim 1, wherein the method comprises:

(a) cloning a DNA molecule into the at least one cloning site in the modified lacZ coding sequence encoding an α-peptide to form recombinant vectors;

(b) introducing the recombinant vectors into host cells, wherein the host cells require α-complementation to produce β-galactosidase activity;

(c) growing the host cells in the presence of a chromogenic substrate or indicator for β-galactosidase activity; and (d) screening for indicia of lac operon marker inactivation.

23. The method according to claim 22, wherein the at least one cloning site has been introduced within a lacZ coding sequence from and including the codon for amino acid 8 to and including the codon for amino acid 38 of β-galactosidase.

24. The method according to claim 22, further comprising adding an inducer of lacZ gene expression when the host cells are grown in the presence of a chromogenic substrate or an indicator of β-galactosidase activity.

25. The method according to claim 22, wherein the method comprises cloning a DNA molecule into a single restriction enzyme site in the modified lacZ coding sequence.

26. The method according to claim 22, wherein the method comprises cloning of a DNA molecule into two restriction enzyme sites in the modified lacZ coding sequence.

27. The method according to claim 22, wherein the method comprises cloning of a DNA molecule into a first restriction enzyme site in the modified lacZ coding sequence; and a second restriction enzyme site which is upstream of the first restriction enzyme site, said second restriction enzyme site being located in the vector sequence.

28. The method according to claim 22, wherein the method comprises cloning of a DNA molecule into a first restriction enzyme site in the modified lacZ coding sequence; and a second restriction enzyme site which is downstream of the first restriction enzyme site, said second restriction enzyme site being located in the vector sequence.

29. The method according to claim 22, wherein the method comprises cloning of a DNA molecule into a first restriction enzyme site which is upstream of the modified lacZ coding sequence, said first restriction enzyme site being located in the vector sequence; and a second restriction enzyme site which is downstream of the modified lacZ coding sequence, said second restriction enzyme site being located in the vector sequence.

* * * * *

UNITED STATES PATENT AND TRADEMARK OFFICE
CERTIFICATE OF CORRECTION

PATENT NO. : 6,127,171
DATED : Oct. 3, 2000
INVENTOR(S) : Slilaty et al.

It is certified that error appears in the above-identified patent and that said Letters Patent is hereby corrected as shown below:

Col. 27, line 42 - "KruI" should be -- NruI --.

Signed and Sealed this

Fifteenth Day of May, 2001

Attest:

NICHOLAS P. GODICI

*Attesting Officer*   Acting Director of the United States Patent and Trademark Office

SEQUENCE LISTING (1) GENERAL INFORMATION:

(iii) NUMBER OF SEQUENCES: 11

(2) INFORMATION FOR SEQ ID NO:1 :

(i) SEQUENCE CHARACTERISTICS:
        (A) LENGTH: 60
        (B) TYPE: amino acid
        (C) TOPOLOGY: linear (ii) MOLECULE TYPE: peptide (iii) SEQUENCE DESCRIPTION: SEQ ID NO:1:

```
Met Thr Met Ile Thr Asp Ser Leu Ala Val Val Leu Gln Arg Arg
                 5                  10                  15

Asp Trp Glu Asn Pro Gly Val Thr Gln Leu Asn Arg Leu Ala Ala
                20                  25                  30

His Pro Pro Phe Ala Ser Trp Arg Asn Ser Glu Glu Ala Arg Thr
                35                  40                  45

Asp Arg Pro Ser Gln Gln Leu Arg Ser Leu Asn Gly Glu Trp Arg
                50                  55                  60
```

(2) INFORMATION FOR SEQ ID NO:2 :

(i) SEQUENCE CHARACTERISTICS:
        (A) LENGTH: 99 nucleotides (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:2 :

TGACCATGAT CACGGACAGC TTAGCCGTCG TTCTGCAGCG TCGCGACTGG          50

GAAAACCCGG GCGTTACCCA GCTGAATCGA TTAGCTGCGC ATCCCCCTT          99

(2) INFORMATION FOR SEQ ID NO:3 :

(i) SEQUENCE CHARACTERISTICS:
        (A) LENGTH: 92 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:3 :

CGCATCCCCC ATTCGCTAGC TGGCGGAATT CCGAAGAGGC GCGCACCGAT          50

AGGCCTTCCC AACAGTTGAG ATCTTTAAAT GGCGAATGGC GC                 92

(2) INFORMATION FOR SEQ ID NO:4 :

(i) SEQUENCE CHARACTERISTICS:
        (A) LENGTH: 100 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:4 :

CAATTTCACA CAGGAGGAAA AAACCATGGT CGACTTAATA CGACTCACTA          50

TAGGGCCTTA TGGGCCCGGT ACCCGGATCC TCGAGAGCTT AGCCGTCGTT         100

(2) INFORMATION FOR SEQ ID NO:5 :

(i) SEQUENCE CHARACTERISTICS:
        (A) LENGTH: 78 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:5 :

TTAAATGGCG AATGGCGGTA AGCTTCGAAC GCGTATGCAT GAGCTCTTAA          50

TTAACTCCGG ATAAATTGTA AGCGTTAA                                 78

(2) INFORMATION FOR SEQ ID NO:6 :

(i) SEQUENCE CHARACTERISTICS:
        (A) LENGTH: 74 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (iv) SEQUENCE DESCRIPTION: SEQ ID NO:6 :

AGCTCTTAAT TAACTCCGGA TCTAGAGCCC GCCTAATGAG CGGGCTTTTT          50

TTTCTTAAGT AAATTGTAAG CGTT                                      74

(2) INFORMATION FOR SEQ ID NO:7 :

(i) SEQUENCE CHARACTERISTICS:
            (A) LENGTH: 372 nucleotides
            (B) TYPE: nucleic acid
            (C) STRANDEDNESS: double-stranded
            (D) TOPOLOGY: circular (ii) MOLECULE TYPE: DNA (iii) HYPOTHETICAL: No (iv) FEATURE: relevant portion of circular molecule listed (v) SEQUENCE DESCRIPTION: SEQ ID NO:7 :

TGTGTGGAAT TGTGAGCGGA TAACAATTTC ACACAGGAGG AAAAAACC ATG        51

GTC GAC TTA ATA CGA CTC ACT ATA GGG CCT TAT GGG CCC GGT         93

ACC CGG ATC CTC GAG AGC TTA GCC GTC GTT CTG CAG CGT CGC        135

GAC TGG GAA AAC CCG GGC GTT ACC CAG CTG AAT CGA TTA GCT        177

GCG CAT CCC CCA TTC GCT AGC TGG CGG AAT TCC GAA GAG GCG        219

CGC ACC GAT AGG CCT TCC CAA CAG TTG AGA TCT TTA AAT GGC        261

GAA TGG CGG TAA GCTTCGAACG CGTATGCATG AGCTCTTAAT               303

TAACTCCTCT AGAGCCCGCC TAATGAGCGG GCTTTTTTTT CTTAAGTAAA         353

TTGTAAGCGT TAATATTTT                                           372

(2) INFORMATION FOR SEQ ID NO:8 :

(i) SEQUENCE CHARACTERISTICS:
            (A) LENGTH: 31 nucleotides
            (B) TYPE: nucleic acid
            (C) STRANDEDNESS: single-stranded
            (D) TOPOLOGY: linear (ii) MOLECULE TYPE: DNA (iii) HYPOTHETICAL: No (iv) SEQUENCE DESCRIPTION: SEQ ID NO:8 :

ACCAATGAAA CCATCTATAG CAGCACCGTA A                              31

(2) INFORMATION FOR SEQ ID NO:9 :

(i) SEQUENCE CHARACTERISTICS:
            (A) LENGTH: 31 nucleotides
            (B) TYPE: nucleic acid
            (C) STRANDEDNESS: single-stranded
            (D) TOPOLOGY: linear (ii) MOLECULE TYPE: DNA (iii) HYPOTHETICAL: No (iv) SEQUENCE DESCRIPTION: SEQ ID NO:9 :

GGAGCAAACA AGAGAGTCGA TGAACGGTAA T                              31

(2) INFORMATION FOR SEQ ID NO:10 :

(i) SEQUENCE CHARACTERISTICS:
        (A) LENGTH: 249 nucleotides
        (B) TYPE: nucleic acid
        (C) STRANDEDNESS: both
        (D) TOPOLOGY: circular (ii) MOLECULE TYPE: DNA (iii) HYPOTHETICAL: No (iv) FEATURE: relevant portion of circular molecule listed (v) SEQUENCE DESCRIPTION: SEQ ID NO:10 :

```
TGTGTGGAAT TGTGAGCGGA TAACAATTTC ACACAGGAAA CAGCT ATG ACC       51

ATG ATC ACG GAC AGC TTA GCC GTC GTT CTG CAG CGT CGC GAC TGG     96

GAA AAC CCG GGC GTT ACC CAG CTG AAT CGA TTA GCT GCG CAT CCC    141

CCA TTC GCT AGC TGG CGG AAT TCC GAA GAG GCG CGC ACC GAT AGG    186

CCT TCC CAA CAG TTG AGA TCT GAG GCC GAT ACT GTC GTC GTC CCC    231

TCA AAC TGG CAG ATG CAC                                        249
```

(2) INFORMATION FOR SEQ ID NO:11 :

(i) SEQUENCE CHARACTERISTICS:
        (A) LENGTH: 375 nucleotides
        (B) TYPE: nucleic acid
        (C) STRANDEDNESS: both
        (D) TOPOLOGY: circular (ii) MOLECULE TYPE: DNA (iii) HYPOTHETICAL: No (iv) FEATURE: relevant portion of circular molecule listed (v) SEQUENCE DESCRIPTION: SEQ ID NO:11 :

```
TGTGTGGAAT TGTGAGCGGA TAACAATTTC ACACAGGAGG AAAAAACCAT      50

GGTCGACTTA ATACGACTCA CTATAGGGCC TTATGGGCCC GGTACCCGGA     100

TCCTCGAGAG CTTAGCCGTC GTTCTGCAGC GTCGCGACTG GGAAAACCCG     150

GGCGTTACCC AGCTGAATCG ATTAGCTGCG CATCCCCCAT TCGCTAGCTG     200

GCGGAATTCC GAAGAGGCGC GCACCGATAG GCCTTCCCAA CAGTTGAGAT     250

CTTTAAATGG CGAATGGCGG TAAGCTTCGA ACGCGTATGC ATGAGCTCTT     300

AATTAACTCC GGATCTAGAG CCCGCCTAAT GAGCGGGCTT TTTTTTCTTA     350

AGGCCGCATC GAATATAACT TCGTA                                375
```